United States Patent [19]

Iwamura et al.

[11] 3,994,932

[45] Nov. 30, 1976

[54] PROCESS FOR THE PREPARATION OF 1-AMINOANTHRAQUINONE

[75] Inventors: Akio Iwamura, Fujisawa; Hisamichi Murakami, Yokohama; Ichiro Okubo, Hachioji, all of Japan

[73] Assignee: Mitsui Toatsu Chemicals, Incorporated, Tokyo, Japan

[22] Filed: Mar. 19, 1975

[21] Appl. No.: 559,984

[30] Foreign Application Priority Data

Apr. 2, 1974 Japan.............................. 49-37162
Apr. 5, 1974 Japan.............................. 49-39149

[52] U.S. Cl............................... 260/378; 260/369
[51] Int. Cl.²....................................... C07C 97/24
[58] Field of Search........................... 260/378, 369

[56] References Cited

UNITED STATES PATENTS

| | | | |
|---|---|---|---|
| 2,860,036 | 11/1958 | Lait..................................... | 260/369 |
| 2,948,739 | 8/1960 | Harris et al........................ | 260/369 |
| 3,433,811 | 3/1969 | Jentzsch............................. | 260/378 |

FOREIGN PATENTS OR APPLICATIONS

| | | |
|---|---|---|
| 2,200,071 | 1972 | Germany |
| 2,340,114 | 1973 | Germany |

OTHER PUBLICATIONS

Fliege et al.; Chemical Abstracts, vol. 79 (1973) No. 136904.

Vorozhtsov et al.; Chemical Abstracts, vol. 55 (1961) column 1547 e–i.

*Primary Examiner*—Arthur P. Demers
*Attorney, Agent, or Firm*—Fisher, Christen & Sabol

[57] ABSTRACT

1-Aminoanthraquinone of high purity is obtained either by catalytically hydrogenating 5-nitro-1,4,4a,9a-tetrahydroanthraquinone dissolved in a polar organic solvent such as methyl cellosolve (i.e., β-hydroxyethyl methyl ether) in the presence of a hydrogenation catalyst such as palladium on carbon or Raney nickel and then treating the resultant hydrogenated product with a base such as sodium hydroxide or pyridine, or by catalytically hydrogenating the 5-nitro-1,4,4a,9a-tetrahydroanthraquinone in the presence of both the hydrogenation catalyst and the base. By the action of the base, the 5-nitro-1,4,4a,9a-tetrahydroanthraquinone nucleus releases hydrogen atoms and is converted to the anthraquinone nucleus, and the released hydrogen serves to reduce the nitro group. Where an excess of hydrogen is introduced into the reaction system for hydrogenation, 1-aminoanthraquinone is further reduced into a leuco type compound thereof which can easily be returned to 1-aminoanthraquinone by oxidation.

16 Claims, No Drawings

PROCESS FOR THE PREPARATION OF 1-AMINOANTHRAQUINONE

BACKGROUND OF THE INVENTION

1. Field of the Invention

This invention relates to a novel process for the preparation of 1-aminoanthraquinone using as starting material 5-nitro-1,4,4a,9a-tetrahydroanthraquinone (hereinafter referred to simply as 5-nitrotetrahydroanthraquinone) expressed by the formula:

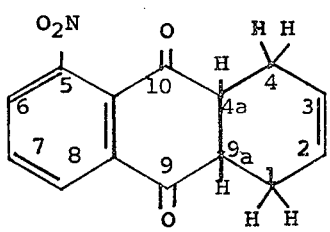

DESCRIPTION OF THE PRIOR ART

1-Aminoanthraquinone is important as an intermediate for anthraquinone disperse dyes, vat dyes and pigments, and has been heretofore synthesized through anthraquinone-1-sulfonic acid obtained by the sulfonation of anthraquinone. However, this prior art process is difficult to practice since it involves the use of a mercury catalyst in the sulfonation step, thus presenting many problems concerning the working environment and environmental pollution. Various methods for the preparation of 1-aminoanthraquinone as alternatives to the above process have been investigated, among which a method of preparation using nitration and reduction reactions of anthraquinone has been assumed to be most effective. However, this method using the niration and reduction of anthraquinone involves the use of large amounts of sulfuric acid and nitric acid, offering problems in handling of the acids and in treatment of the resultant waste liquor. Additionally, 1-aminoanthraquinone obtained by this method contains a large quantity of by-products including diamino compounds and the 2-amino compound, and must essentially be purified by complicated operations for use as an intermediate of dye. Thus, this method is not successful from the industrial point of view.

There have also been proposed several process for the preparation of 1-nitroanthraquinone wherein 5-nitro-1,4-naphthoquinone (hereinafter referred to simply as 5-nitronaphthoquinone) is condensed with 1,3-butadiene to give 5-nitrotetrahydroanthraquinone, followed by oxidation to obtain 1-nitroanthraquinone. For example, according to N. N. Woroshtzov et al. (Khim. Nauka i Prom, 5, 474–475, 1960) 1-nitroanthraquinone can be obtained by condensing 5-nitronaphthoquinone and 1,3-butadiene in ethanol and oxidizing the resultant condensation product with air in an alcoholic alkali solution. Moreover, French Pat. No. 1,486,803 (Institut Premyslu Organiznco) describes a process for the preparation of 1-nitroanthraquinone by reacting butadiene with 5-nitronaphthoquinone in nitrobenzene and oxidizing the resultant reaction product by means of nitrobenzene in the presence or absence of piperidine without isolation of the reaction product. 1-Nitroanthraquinone obtained by these processes can be readily converted into 1-aminoanthraquinone by an ordinary reduction method. However, these processes have a vital disadvantage in that when 5-nitrotetrahydroanthraquinone which is obtained by condensation of 5-nitronaphthoquinone and 1,3-butadiene is dissolved in a suitable solvent after isolation thereof, or as it is without isolation, and then air is fed into the solution for oxidation in the presence of a base such as piperidine, various by-products are also produced, so that 1-aminoanthraquinone obtained by reduction of the resultant 1-nitronaphthoquinone with the various by-products is low in purity. As a result, it is difficult to use such 1-aminoanthraquinone as an intermediate for dyes.

SUMMARY OF THE INVENTION

It is a primary object of the present invention to provide a novel process for preparing 1-aminoanthraquinone from starting 5-nitrotetrahydroanthraquinone.

It is another object of the present invention to provide a process for preparing, from 5-nitrotetrahydroanthraquinone, 1-aminoanthraquinone of high purity which can be used, as it is, as an intermediate for dyes or other substances.

The above objects can be achieved by either (1) catalytically hydrogenating 5-nitrotetrahydroanthraquinone in a polar organic solvent in the presence of a hydrogenation catalyst and adding a base to the resultant reaction solution for further reaction, or (2) catalytically hydrogenating 5-nitrotetrahydroanthraquinone in a polar organic solvent in the presence both of a hydrogenation catalyst and a base. In other words, the process of the present invention involves the following two reactions, i.e., (A) a catalytic hydrogenation reaction and (B) the reaction occurring in the presence of a base. In the above embodiment (1), reaction (A) is completed in a reaction system and then reaction (B) is carried out in the reaction system to which is added a base. On the other hand, in embodiment (2), reactions (A) and (B) proceed in the same reaction system.

In either of the above embodiments (1) or (2) of the present invention, there occur, at the same time, reduction of the nitro group of 5-nitrotetrahydroanthraquinone to the amino group and the dehydrogenation of the tetrahydroanthraquinone nucleus, thereby giving 1-aminoanthraquinone as a reaction product. In this connection, it has been found that a characteristic reaction takes place in the reaction system, i.e., the hydrogen released from the tetrahydroanthraquinone nucleus is effectively consumed by the action of the base for reducing the nitro group to an amino group as will be described in detail hereinafter. This reaction is herein referred to as a self oxidation and reduction reaction. Such a self oxidation and reduction reaction which has not previously been known in the art was discovered as a result of the study leading to the process of the present invention.

It will be noted that even though, in embodiment (1) or (2), 5-Nitrotetrahydroanthraquinone may be reduced up to a leuco type compound of 1-aminoanthraquinone having the formula:

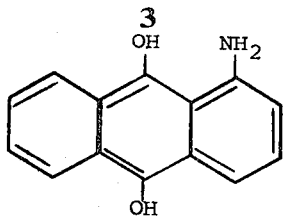

by means of an excess of hydrogen introduced, the leuco type compound can be readily converted to 1-aminoanthraquinone by oxidation.

DESCRIPTION OF THE PREFERRED EMBODIMENTS

In order to facilitate understanding of the process of the present invention, the characteristic reaction will be more particularly illustrated hereinafter based on experiments conducted by the present inventors.

With embodiment (1), the nitro group in a 5-nitrotetrahydroanthraquinone molecule is reduced by catalytic hydrogenation to an amino group or its intermediate of a hydroxylamino group or a nitroso group. After completion of the catalytic hydrogenation, the tetrahydroanthraquinone nucleus is allowed to release hydrogen and to be converted to an anthraquinone nucleus by the action of a base, during which the hydroxylamino group or the nitroso group is in turn converted to an amino group by means of the released hydrogen atoms. If hydrogen exists in excess in the reaction system, it is assumed that 5-nitrotetrahydroanthraquinone is converted to a leuco type compound of 1-aminoanthraquinone or of 5-amino-1,4-dihydroanthraquinone. That is, if 1 mol of 5-nitrotetrahydroanthraquinone is allowed to absorb 3 mols of hydrogen, there can be obtained as a product 5-aminotetrahydroanthraquinone. The product can be converted to 1-aminoanthraquinone by subjecting it to further reaction in the presence of a base followed by absorption of 1 mol proportion of oxygen therein (see Example 2 hereinbelow). Furthermore, where hydrogen is allowed to be absorbed in a 2 mols proportion, 5-hydroxylaminotetrahydroanthraquinone is obtained as the hydrogenation product which, when treated in the presence of a base, is formed into a leuco type compound of 1-aminoanthraquinone as the result of intramolecular or intermolecular rearrangement of hydrogen. The leuco type compound is readily converted to 1-aminoanthraquinone by absorbing 0.5 mol proportion of oxygen (see Example 1 hereinbelow). Moreover, where 1 mol proportion of hydrogen is absorbed, there is obtained an intermediate product which is assumed to be 5-nitrosotetrahydroanthraquinone. The intermediate product is converted to 1-aminoanthraquinone by the action of a base.

From the above facts, it will be clear that the product obtained as a result of the catalytic hydrogenation of 5-nitrotetrahydroanthraquinone is subjected to an intramolecular or intermolecular rearrangement of hydrogen or to a self oxidation and reduction reaction by the action of a base to form 1-aminoanthraquinone or its leuco type compound.

With embodiment (2), it is assumed that when 5-nitrotetrahydroanthraquinone is treated with a base, the intramolecular or intermolecular rearrangement of hydrogen takes place, so that the tetrahydro nucleus is dehydrogenated and the nitro group is reduced to form 1-hydroxylaminoanthraquinone, which is then catalytically hydrogenated to give 1-aminoanthraquinone (see Example 10 hereinafter). This self oxidation and reduction reaction is considered to proceed at a very high rate due to the fact that the addition of a strong base to a 5-nitrotetrahydroanthraquinone solution at room temperature results immediately in the formation of a green alkali salt of 1-hydroxylaminoanthraquinone. Although there is no doubt that the above reaction occurs as a main reaction, there is the possibility that other reactions take place depending on reaction conditions, including a reaction in which a product of partial reduction of the nitro group of 5-nitrotetrahydroanthraquinone is self oxidized and reduced by means of a base.

In embodiment (2), it is certain that the self oxidation and reduction of 5-nitrotetrahydroanthraquinone contributes to the formation of 1-aminoanthraquinone. This is supported by the fact that when about 1 mol of hydrogen per mol of 5-nitrotetrahydroanthraquinone is introduced into the reaction system from the outside, 1-aminoanthraquinone is produced in an almost quantitative manner (see Example 19 hereinbelow). In general, the reduction of one nitro group to an amino group necessitates six hydrogen atoms from a theoretical point of view. However, in the reaction of embodiment (2), only two fresh hydrogen atoms are required for the reaction, so that it is considered apparent that the remaining four hydrogen atoms are supplied from a tetrahydro nucleus of the starting material. In practice, the absorption of hydrogen does not stop at 1 mol per mol of the starting 5-nitro compound and 2 or greater mols of hydrogen are absorbed especially under vigorous reaction conditions. The absorption of 2 mols of hydrogen per mol of the 5-nitro compound results in the formation of a leuco type compound (or a hydroquinone compound) of 1-aminoanthraquinone, which is readily oxidized to 1-aminoanthraquinone with air. Where greater than 2 mols of hydrogen per mol of the 5-nitro compound is absorbed in the reaction of embodiment (2), over-reduced materials having unknown structures are secondarily produced and are not necessarily returned to 1-aminoanthraquinone by oxidation.

5-Nitrotetrahydroanthraquinone used as the starting material in the process of the present invention can be obtained by a Diels-Alder condensation of 5-nitro-1,4-naphthoquinone and 1,3-butadiene. 5-Nitro-1,4-naphthoquinone can be easily obtained by nitrating 1,4-naphthoquinone in sulfuric acid by means of nitric acid, and may be used not only after purification, but also as the crude reaction product which contain impurities such as 6-nitro compound in an amount as great as 1–20%.

The Diels-Alder condensation of 5-nitro-1,4-naphthoquinone and 1,3-butadiene is operable at from room temperature to 200° C. in a suitable solvent, e.g.: alcohols such as mthanol, ethanol, propanol, isopropanol, butanol, isobutanol and the like, cyclohexanols such as cyclohexanol, alkyl-substituted cyclohexanols and the like; glycols such as ethylene glycol, propylene glycol, dipropylene glycol and the like; glycol ethers such as methyl cellosolve (i.e., β-hydroxyethyl methyl ether), ethyl cellosolve (i.e., β-hydroxydiethyl ether), diethylene glycol monomethyl ether, diethylene glycol monoethyl ether, methoxybutanol and the like; aromatic compounds such as benzene, toluene, chlorobenzene, dichlorobenzene, nitrobenzene and the like; amides such as dimethylformamide, dimethylacetamide and the like; and other compounds such as ethyl acetate, butyl acetate, dioxane and the like. The condensation reaction may be effected in the presence of a catalyst such as trichloroacetic acid or trimethylamine or a catalyst for Friedel-Crafts reactions such as aluminum chloride.

The 5-nitrotetrahydroanthraquinone obtained in the above manner can be used in the reaction of embodiment (1) or (2) after isolation thereof from the reaction system, or can be used, without isolation, in the form of the reaction solution obtained after the Diels-Alder condensation reaction.

The catalytic hydrogenation and subsequent base treatment of 5-nitrotetrahydroanthraquinone, i.e., embodiment (1), are practiced by the present invention in the following manner:

5-nitrotetrahydroanthraquinone is dissolved or suspended in a polar organic solvent and a hydrogen gas is fed into the solution or suspension in the presence of a hydrogenation catalyst. The polar organic solvent used herein is required to be inert to the hydrogenation reaction. Examples of polar organic solvents which satisfy the above requirement are: alcohols such as methanol, ethanol, propanol, isopropanol, butanol, isobutanol and the like; cyclohexanols such as cyclohexanol, alkylsubstituted cyclohexanols and the like; glycols such as ethylene glycol, propylene glycol, dipropylene glycol and the like; glycol ethers such as methyl cellosolve (i.e., $\beta$-hydroxyethyl methyl ether), ethyl cellosolve (i.e., $\beta$-hydroxydiethyl ether), diethylene glycol monoethyl ether, diethylene glycol monoethylether, methoxybutanol and the like; amides such as dimethylformamide, dimethylacetamide and the like; and other compounds such as ethyl acetate, butyl acetate, dioxane and the like. These polar organic solvents may be used singly or in combination and are employed in an amount of 5 to 100 parts by weight, preferably 10 to 50 parts by weight per part of 5-nitrotetrahydroanthraquinone.

The hydrogenation catalysts of the present invention are those which are generally employed for catalytically reducing a nitro compound to an amino compound and which contain as effective component, for example, palladium, platinum, ruthenium, rhodium, nickel, cobalt, copper or the like. Especially, a noble metal catalyst supported on a carrier such as carbon, alumina, diatomaceous earth or the like, or a Raney-nickel catalyst is suitable for the purpose of the present invention. The amount of catalyst, generally between about 0.002 and 20 parts by weight per 100 parts of the 5-nitro compound, will vary to a considerable extent depending upon the kind of catalyst, its activity, the concentration of the effective component on a carrier where a carrier is used, and the like. When the reaction is effected by the use of a noble metal catalyst applied onto a carrier, it is preferred to use 0.002 to 0.5 parts by weight of catalyst (calculated in terms of the noble metal), with a catalyst of a noble metal without use of a carrier such as palladium black, the amount is preferably within the range of 0.01 to 5 parts by weight of the catalyst, and with a nickel, cobalt, copper or copper-chromium catalyst, the amount is preferably within the range of 0.05 to 20 parts by weight (in terms of metal), each per 100 parts of 5-nitrotetrahydroanthraquinone.

The reaction temperature may be within a wide range of from 0° to 160° C. since the catalytic hydrogenation reaction involves little or no side reactions adversely affecting the main reaction. However, the reaction temperature is preferably within the range of 10° to 120° C. for convenience of reaction operations. The reaction may be carried out either under normal atmospheric pressure or under an elevated pressure up to about 100 kg/cm$^2$ if necessary.

In the catalytic hydrogenation reaction under the above reaction conditions, 1 to 3 mols, preferably 1.5 to 2.5 mols, of hydrogen is allowed to be absorbed in 1 mol of 5-nitrotetrahydroanthraquinone.

As already described hereinbefore, the theoretical amount of hydrogen to be absorbed so as to obtain 1-aminoanthraquinone quantitatively is 1 mol per mol of 5-nitrotetrahydroanthraquinone. However, if the absorption of hydrogen is stopped at 1 mol per mol of the 5-nitro compound, a slight amount of an intermediate remains in the reaction system so that 1-aminoanthraquinone is lowered in purity. Therefore, from 1 to 3 mols of hydrogen per mol of the 5-nitro compound are used for absorption in the process of this embodiment of the present invention. However, absorption of more than 3 mols of hydrogen per mol of the 5-nitro compound would have no appreciable effect on the result. The time required for the absorption of hydrogen is ordinarily from 0.5 to 20 hours.

After completion of the catalytic hydrogenation reaction, a base is added to the reaction solution for the self oxidation and reduction reaction. In this connection, the hydrogenation catalyst may be removed by filtration either before the addition of a base to the reaction solution or after the reaction with the base. Although all ordinary bases may be employed as a base useful in the present invention, the following bases are particularly preferred: oxides, hydroxides, carbonates, bicarbonates, phosphates and acetates of alkali and alkaline earth metals such as potassium, sodium, calcium and the like; and ammonia and organic amines such as diethylamine, triethylamine, morpholine, piperidine and the like. These bases are generally employed in an amount of from 0.01 to 10 mols per mol of 5-nitrotetrahydroanthraquinone. In order to suppress side reactions and to effect the reaction smoothly, the amount of base is preferably in the range of 0.5 to 3 mols per mol of the 5-nitro compound. The bases may be used singly or in combination. The base may be added to the reaction solution as it is or may be added after dissolution thereof in water, an alcohol or other polar organic solvent, if desired.

The self oxidation and reduction reaction by a base may be effected in a wide temperature range of from 0° to 250° C. However, the reaction temperature is preferably in the range of greater than room temperature, e.g. from about 20° C., to less than the boiling point of the polar organic solvent employed from the viewpoint of reaction operation. Furthermore, the reaction is generally carried out under normal atmospheric pressure but may be effected under an elevated pressure up to 100 kg/cm$^2$, if required. The self oxidation and reduction reaction proceeds relatively rapidly in the above-described temperature range and is generally completed within 20 hours. Moreover, the reaction may be completed within 3 hours under more preferable reaction conditions.

In cases where the reaction solution obtained by catalytically hydrogenating the starting material, followed by self oxidation and reduction reaction with a base still contains the hydrogenation catalyst therein, the catalyst must be removed by filtration. The resultant reaction solution is cooled or concentrated as it is or after being neutralized with a suitable acid, or is diluted with a non solvent for 1-aminoanthraquinone to separate 1-aminoanthraquinone as crystals, followed by filtration and drying to obtain 1-aminoanthraquinone. When hydrogen is absorbed in an amount greater than the theoretical during the reaction, part of the thus obtained 1-aminoanthraquinone is converted to a leuco type compound thereof. Accordingly, before separation of 1-aminoanthraquinone, it is preferable to inject air or oxygen into the reaction solution or to add to the solution an oxidizing agent such as hydrogen peroxide in a temperature range of from 0° to 150° C. for converting the leuco type compound to 1-aminoanthraquinone thereby to obtain a product of high purity. The amount of oxidizing agent required for the oxidation can be readily calculated from the amount of hydrogen absorbed. When the reaction is conducted on a small scale, the oxidation reaction proceeds in a satisfactory manner by merely allowing the reaction solution to stand in air for a period of time for contact with the air after completion of the self oxidation and reduction reaction with a base. In this way, 1-aminoanthraquinone of high purity can be obtained.

When the hydrogenation is conducted in the presence of a base, i.e., with embodiment (2), the reaction is carried out in a polar organic solvent in the presence of both a hydrogenation catalyst and a base while feeding hydrogen into the reaction system. This reaction involves no substantial concurrent side reactions, so that limitation of the reaction temperature to suppress side reactions is unnecessary. In general, the reaction temperature may be in a wide range of from 0° to 160° C., and is preferably in the range of 10° to 120° C. for convenience of the reaction operation. The reaction is operable under normal atmospheric pressure and it may also be effected under an elevated pressure of up to 100 kg/cm$^2$, if necessary or desired.

The polar organic solvent, hydrogenation catalyst and base herein used and the amounts thereof are each the same as for embodiment (1). In this embodiment, 1 mol of 5-nitrotetrahydroanthraquinone is allowed to absorb 1 to 3 mols (preferably 1.1 to 2.2 mols) of hydrogen, followed by separation of the catalyst by filtration. Although the time required for absorbing a predetermined amount of hydrogen will vary depending upon reaction conditions including reaction temperature, amount of hydrogenation catalyst, concentration of 5-nitrotetrahydroanthraquinone and the like, it is generally within the range of 0.5 to 20 hours and may be within the range of 1 to 6 hours under more preferable reaction conditions.

In the reaction of this embodiment, four hydrogen atoms of the tetrahydro nucleus of 5-nitrotetrahydroanthraquinone are also likely to contribute to the reduction of the nitro group. The amount of hydrogen required for obtaining 1-aminoanthraquinone stoichiometrically is 1 mol per mol of the starting material. As will be shown in Example 19, in fact, though the absorption of about 1 mol of hydrogen results in the almost quantitative formation of 1-aminoanthraquinone, there is a tendency that a small amount of an intermediate, particularly 1-hydroxylaminoanthraquinone, will still remain in the reaction system under such conditions. Accordingly, a product of high purity is easier to obtain by allowing the starting material to absorb therein 1.1 to 2.2 mols of hydrogen for reducing a portion or substantially all thereof to leuco-1-aminoanthraquinone. In this case, after completion of the hydrogenation, air or oxygen, or an oxidizing agent such as hydrogen peroxide is added at a temperature of 0° C, to 150° C. to the reaction solution. The catalyst may be separated by filtration or it may be allowed to remain in order to convert the leuco type compound to 1-aminoanthraquinone. However, with a reaction on a small scale in which only a small amount of reaction solution is handled, the oxidation reaction proceeds satisfactorily by allowing the reaction solution to stand in air after completion of the hydrogenation reaction.

As described hereinbefore, when greater than 2 mols of hydrogen per mol of the starting 5-nitro compound is absorbed, over-reduced materials which cannot be returned or converted to 1-aminoanthraquinone by oxidation in a complete manner are also secondarily produced in the reaction of this embodiment.

However, a suitable selection of reaction conditions (including kinds of solvent, base and catalyst, reaction temperature and the like) makes it possible to stop the absorption of hydrogen at 2 mols per mol of the starting material. Especially when there is added greater than 0.5 mol of alkali hydroxide per mol of the starting 5-nitro compound, it has been found that hydrogen is not absorbed in an amount greater than 2 mols, and the formation of over-reduced by-products which would result from further hydrogenation of leuco-1-aminoanthraquinone does not occur. This is a prominent feature of the present invention.

After completion of the reaction, the reaction solution from which the catalyst is removed by filtration is subjected, with or without neutralization by an acid, to cooling, condensation, or dilution for crystallization. The resultant crystals are separated by filtration and dried to obtain 1-aminoanthraquinone of high purity.

As illustrated hereinbefore, there is provided in the present invention a novel process for the preparation of 1-aminoanthraquinone by catalytically hydrogenating 5-nitrotetrahydroanthraquinone in a polar organic solvent, followed by self oxidation and reduction with a base. In this process, it is apparent that the self oxidation and reduction of the 5-nitro compound by means of a base plays an important role in the preparation of 1-aminoanthraquinone.

A prominent advantage of the present invention resides in that when compared with known processes for the preparation of 1-aminoanthraquinone wherein anthraquinone is first nitrated and then reduced and wherein 5-nitrotetrahydroanthraquinone is oxidized to form 1-nitroanthraquinone followed by reduction to obtain 1-aminoanthraquinone, the process of the present invention has a small number of simple steps and ensures the formation of 1-aminoanthraquinone of higher purity at higher yield. The highly pure 1-aminoanthraquinone obtained may be used with or without purification as an intermediate for dyes.

Another advantage of the present invention is that hydrogen atoms of the starting 5-nitro compound are effectively utilized for the reduction of the nitro group since the process of the present invention is primarily based upon the self oxidation and reduction reaction. In addition, all of the steps of the present invention beginning with the Diels-Alder condensation of 5-nitro-1,4-naphthoquinone and 1,3-butadiene are operable in the same solvent. Thus, the present invention has remarkably high industrial merit in comparison with the known processes for the preparation of 1-aminoanthraquinone.

The present invention is not limited by but will be particularly illustrated in the following examples wherein all parts are parts by weight unless otherwise indicated.

EXAMPLE 1

2.6 Grams of 5% palladium on carbon catalyst was added to a mixture of 260 grams of 5-nitrotetrahydroanthraquinone and 24,000 grams of ethanol, into which was injected hydrogen for absorption in the 5-nitro compound in an amount of 2 mols per mol of the 5-nitro compound at normal (ambient) temperature and under normal atmospheric pressure. The solution which was first pale yellow turned reddish brown in color as the reaction proceeded and a small amount of precipitate appeared in the solution. When the hydrogenation was continued, the solution became almost transparent and dark reddish brown upon completion of the reaction. The hydrogen in the reactor was replaced by nitrogen, to which was added 400 grams of a 20% sodium hydroxide solution and the color of the resultant solution turned dark yellowish brown immediately after the addition of the alkali during which a small amount of glossy crystals were precipitated. The reaction was completed immediately, dark yellowish brown being the color of leuco-1-aminoanthraquinone which is obtained by catalytical hydrogenation of 1-aminoanthraquinone or by having 1 mol of hydrogen absorbed in 1 mol of 1-aminoanthraquinone under the same reaction conditions, and then air was fed into the solution for oxidation. Upon determination, it was found that 0.5 mol of oxygen was absorbed per mol of the 5-nitro compound. As a result, the reaction solution turned reddish orange with a precipitate of a reddish orange color. The resultant solution was subjected to filtration, followed by extraction of the cake with acetone for separation of the catalyst. The resultant filtrate was dried up to obtain 220 grams of 1-aminoanthraquinone having a purity of 98%.

The above process was repeated except that the catalyst was separated by filtration prior to the addition of sodium hydroxide. The resultant filtrate was dried to obtain a solid substance which was then subjected to analyses of infrared spectrum, NMR (nuclear magnetic resonance) using $CDCl_3$ as solvent, and MS spectrum, revealing that the substance was 5-hydroxylamino-1,4,4a,9a-tetrahydroanthraquinone.

The analytical data were as follows:
IR: 3400, 3300, 1670, 1650, 1590, and 1250 $cm^{-1}$
NMR $\tau$ values: 7.7, 6.7, 4.3, 3.5 and 2.1–2.7 ppm
MS, m/e: 257, 243, 227 and 225

EXAMPLE 2

0.13 Gram of a 5% palladium on carbon catalyst was added to a mixture of 13 grams of 5-nitrotetrahydroanthraquinone and 1200 grams of ethanol, and hydrogen was fed into the resultant mixture for absorption in an amount of 3 mols per mol of the 5-nitro compound at room temperature and under atmospheric pressure. The solution was first pale yellow in color, and then gradually turned yellowish brown and finally pale yellow again. Then, after the hydrogen in the reactor was replaced by nitrogen, 20 grams of a 20% sodium hydroxide solution was added to the reaction solution, the color of which immediately turned dark reddish brown through dark reddish purple and a small amount of glossy crystals were precipitated. The reaction was completed rapidly and air was fed into the reaction solution for oxidation. Upon determination, it was found that 1 mole of oxygen was absorbed per mol of the 5-nitro compound. As a result of the oxidation, the reaction solution turned reddish orange with reddish orange-colored crystals being precipitated. The resultant solution was subjected to filtration, followed by extraction of the resultant cake with acetone for separation of the catalyst. The resultant filtrate was dried to obtain 11 grams of 1-aminoanthraquinone having a purity of 95%.

The above process was repeated except that prior to addition of sodium hydroxide to the reaction solution, the catalyst was removed by filtration and the resultant filtrate was dried to obtain a solid substance. The thus obtained substance was subjected to infrared spectrum and MS spectrum analyses, revealing that the same was 5-amino-1,4,4a,9a-tetrahydroanthraquinone. The analytical data were as follows:
IR: 3420, 3300, 1690, 1620, 1275 and 1240 $cm^{-1}$
MS, m/e: 227, 212, 209, 199 and 180

EXAMPLE 3

6.1 Grams of 5-nitro-1,4-naphthoquinone, 140 grams of methyl cellosolve (i.e., $\beta$-hydroxyethyl methyl ether) and 2.4 grams of 1,3-butadiene were introduced into an autoclave and heated to 80° C. for reaction for 2.5 hours. After allowing to cool, 0.06 gram of a 5% palladium on carbon catalyst was added to the solution into which was fed hydrogen while agitating at room temperature under normal pressure for hydrogen absorption in the amount of 2 mols per mol of the starting 5-nitro material. Thereafter, the catalyst was separated by filtration. To the resultant filtrate was added 6 grams of a 20% aqueous sodium hydroxide solution, which was agitated at 60° C. for 1.5 hours for reaction. After completion of the reaction, hydrochloric acid was added to the reaction solution for neutralization, followed by removing methyl cellosolve by distillation under a reduced pressure of 0.2 $kg/cm^2$ for concentration. The thus concentrated solution was allowed to cool thereby to obtain crystals of 1-aminoanthraquinone. After separation by filtration, the crystals were washed with water and dried to obtain 5.6 grams of 1-aminoanthraquinone having a purity of 98.5%.

The above process was repeated except that sodium hydroxide was added to the solution for reaction after completion of the hydrogenation and then the catalyst was separated by filtration. Similar results were obtained.

EXAMPLE 4

122 Grams of 5-nitro-1,4-naphthoquinone which contained 10% of the 6-nitro compound, 1000 grams of ethanol, and 48 grams of 1,3-butadiene were introduced into an autoclave and subjected to condensation reaction at 80° C. for 2.5 hours with agitation. The resultant reaction solution was allowed to cool to precipitate crystals, which were then separated by filtration and dried to obtain 114 grams of the condensation product of 5-nitro-1,4,4a,9a-tetrahydroanthraquinone. The thus obtained product was charged into 2800 grams of methyl cellosolve, to which was added 1.2 grams of 5% palladium on carbon catalyst, followed by feeding thereinto hydrogen for hydrogenation under room temperature and normal pressure conditions to absorb hydrogen in an amount of 2 mols per mol of the crude 5-nitro compound. Then, the catalyst was removed by filtration and 24 grams of piperidine was added to the resultant filtrate. The resultant solution was heated to 110° C. and air was injected for oxidation at 110° C. to 120° C for 2 hours. Then, the reaction solution was subjected to distillation to remove solvent until crystals began to precipitate. The resultant solution was allowed to cool, followed by separation of crystals therefrom and drying to obtain 90 grams of 1-aminoanthraquinone containing therein 1% of 2-aminoanthraquinone.

EXAMPLE 5

0.1 Gram of 5% palladium on carbon catalyst was added to a mixture of 12.8 grams of 5-nitrotetrahydroanthraquinone and 170 grams of dipropylene glycol in an autoclave. Hydrogen was injected up to a pressure of 25 kg/cm$^2$ while agitating the mixture at 120° C. for hydrogenation of the nitro compound, with the result that 2 mols of hydrogen were absorbed per mol of the starting nitro compound. The resultant reaction solution was subjected to filtration at 120° C. to 130° C. for separation of the catalyst therefrom. To the resultant filtrate was added 10 grams of 20% aqueous sodium hydroxide solution while agitating at 130° C. for 1 hour, followed by dilution thereof with 350 grams of water to obtain crystals. The thus obtained crystals were separated by filtration, washed with water and dried to yield 9.8 grams of 1-aminoanthraquinone having a purity of 96.5%.

The above process was repeated except that after completion of the hydrogenation, sodium hydroxide was added to the solution for reaction and then the catalyst was removed by filtration under hot conditions, followed by dilution with water. Similar results were obtained.

EXAMPLE 6

122 Grams of 5-nitro-1,4-naphthoquinone which contained 10% of the 6-nitro compound, 2800 grams of methyl cellosolve and 48 grams of 1,3-butadiene were charged into an autoclave and reacted at 90° C. for 2 hours. The reaction solution was allowed to stand for cooling and 1.2 grams of a 5% palladium on carbon catalyst was added thereto. Thereafter, the procedure of Example 4 was repeated to obtain 104 grams of 1-aminoanthraquinone containing therein 7% of 2-aminoanthraquinone.

EXAMPLE 7

0.07 Gram of 5% palladium on carbon catalyst was added to a mixture of 7.7 grams of 5-nitrotetrahydroanthraquinone and 240 grams of butanol, which was then heated up to 50° C. Hydrogen was then fed into the solution under normal pressure to absorb hydrogen in an amount of 2 mols per mol of the starting 5-nitro compound. After separation of the catalyst by filtration, 4.0 grams of crystal sodium carbonate was added to the reaction solution while agitating at a temperature of 100° C. for 1 hour. Thereafter, hydrochloric acid was added to the reaction solution for neutralization, then butanol was distilled off from the solution until crystals began to precipitate. After allowing to cool, the reaction solution was filtered and the crystals were washed with water and dried to obtain 6.0 grams of 1-aminoanthraquinone having a purity of 97.2%.

When the above process was repeated using sodium phosphate instead of sodium carbonate, similar results were obtained.

EXAMPLE 8

1.4 Grams of a palladium on carbon catalyst was added to a mixture of 154 grams of 5-nitrotetrahydroanthraquinone and 3000 grams of methyl cellosolve, into which was fed hydrogen at room temperature under normal pressure for hydrogenation. After hydrogen was absorbed in an amount of 2 mols per mol of the 5-nitro compound, the catalyst was separated by filtration. To the resultant filtrate was added 60 grams of triethylamine, followed by agitating at 100° C. for 3 hours and feeding air at 100° C. for 1 hour. Then, methyl cellosolve was removed by distillation until crystals began to precipitate. The solution was allowed to cool and the crystals were separated by filtration, washed with water and dried to obtain 118 grams of 1-aminoanthraquinone having a purity of 98.0%.

EXAMPLE 9

To a mixture of 12.8 grams of 5-nitrotetrahydroanthraquinone and 170 grams of cyclohexanol was added 0.3 gram of a Raney-nickel catalyst. Then, hydrogen was fed into the mixture while agitating at 100° C. for hydrogenation. After hydrogen was absorbed in an amount of 2 mols per mol of the nitro compound, the catalyst was separated by filtration. To the resultant filtrate was added 10 grams of a 20% aqueous sodium hydroxide solution, followed by agitating at 100° C. for 1 hour. Then, the reaction solution was cooled to 10° C. to precipitate crystals which were separated by filtration, washed with water and dried to obtain 9.2 grams of 1-aminoanthraquinone having a purity of 98%.

EXAMPLE 10

To a mixture of 260 grams of 5-nitrotetrahydroanthraquinone and 10,100 grams of methyl cellosolve were added 2.6 grams of a 5% palladium on carbon catalyst and 300 grams of a 20% aqueous sodium hydroxide solution, followed by agitating at room temperature for 1 hour. The color of the solution was green inherent to 1-hydroxylaminoanthraquinone. Part of the reaction solution was sampled and subjected to a thin layer chromatography, by which it was recognized that almost all of the starting 5-nitro compound was converted to 1-hydroxylaminoanthraquinone. Thereafter, hydrogen was fed into the reaction solution for hydrogenation and 2 mols of hydrogen was absorbed in each 1 mol of the 5-nitro compound. The hydrogen in the reactor was replaced by nitrogen, followed by introduction of air into the reaction solution for oxidation. Upon determination, it was found that oxygen was absorbed in an amount of 0.5 mol per mol of the 5-nitro compound. The reaction solution turned reddish orange with a reddish orange precipitate. The precipitate was separated by filtration, washed with water and dried to obtain 220 grams of 1-aminoanthraquinone having a purity of 98%.

EXAMPLE 11

2.6 Grams of a palladium on carbon catalyst and 300 grams of a 20% aqueous sodium hydroxide solution were added to a mixture of 260 grams of 5-nitrotetrahydroanthraquinone and 10,100 grams of methyl cellosolve. The color of the resultant solution was green. Immediately after the addition of the sodium hydroxide solution, hydrogen was fed into the solution for absorbing hydrogen in an amount of 2 mols per mol of the 5-nitro compound. The reaction solution was reddish orange when hydrogen was absorbed in a 1 mol proportion, with a substantial amount of needle-like crystals being precipitated, but when hydrogen was absorbed in a 2 mol proportion, the same changed into a dark brown suspension the color of which was almost the same as that obtained by having a 1 mol proportion of hydrogen absorbed in 1-aminoanthraquinone under the same reaction conditions. Then, the procedure of Example 10 was repeated to obtain results similar to those of Example 10.

EXAMPLE 12

6.1 Grams of 5-nitro-1,4-naphthoquinone, 140 grams of methyl cellosolve 2.4 grams of 1,3-butadiene were introduced into an autoclave, heated up to 80° C. and reacted for 2.5 hours. After the reaction solution was allowed to cool, 0.06 gram of a 5% palladium on carbon catalyst and 6 grams of a 20% aqueous sodium hydroxide solution were added to the solution, into which was fed hydrogen at room temperature under normal pressure with agitation to absorb hydrogen in the 5-nitro-1,4-naphthoquinone in an amount of 2 mols per mol of the nitro compound. Then, the catalyst was removed by filtration and hydrochloric acid was added to the resultant filtrate for neutralization. From the thus neutralized solution was removed methyl cellosolve by distillation for concentration, followed by allowing to cool to precipitate crystals. The crystals were separated by filtration, washed with water and dried to obtain 5.8 grams of 1-aminoanthraquinone with a purity of 98.7%.

EXAMPLE 13

122 Grams of 5-nitro-1,4-naphthoquinone which contained 10% of the 6-nitro compound, 1,000 grams of ethanol and 48 grams of 1,3-butadiene were placed in an autoclave, followed by reaction at 80° C. for 2.5 hours. After the solution was allowed to cool for precipitating crystals, the crystals were separated by filtration, washed with water and dried to obtain 114 grams of 5-nitro-1,4,4a,9a-tetrahydroanthraquinone. The thus obtained nitro compound was introduced into 2,800 grams of methyl cellosolve, to which was added 1.2 grams of a 5% palladium on carbon catalyst and 120 grams of a 20% aqueous sodium hydroxide solution, followed by feeding hydrogen thereinto for hydrogenation while agitating at room temperature and under normal pressure to absorb hydrogen in an amount of 2 mols per mol of the crude 5-nitro compound. Thereafter, the catalyst was separated by filtration and air was injected to the resultant filtrate for oxidation at room temperature for 3 hours. Then, the methyl cellosolve was distilled off from the reaction solution until crystals were precipitated, followed by allowing to cool. The thus precipitated crystals were separated by filtration, washed with water and dried to obtain 92 grams of 1-aminoanthraquinone containing therein 1% of 2-aminoanthraquinone.

EXAMPLE 14

122 Grams of 5-nitro-1,4-naphthoquinone which contained 10% of the 6-nitro compound, 2,800 grams of methyl cellosolve and 48 grams of 1,3-butadiene were placed in an autoclave, followed by reaction at 90° C. for 2 hours. After allowing to cool, 1.2 grams of a 5% palladium on carbon catalyst and 120 grams of a 20% aqueous sodium hydroxide solution were added to the reaction solution. Then, the procedure of Example 13 was repeated to obtain 108 grams of 1-aminoanthraquinone containing 7% of 2-aminoanthraquinone.

EXAMPLE 15

0.07 Gram of 5% palladium on carbon catalyst and 8 grams of crystal sodium carbonate were added to a mixture of 7.7 grams of 5-nitrotetrahydroanthraquinone and 320 grams of butanol. The resultant mixture was heated to 70° C. and hydrogen was fed for hydrogenation under normal pressure to have hydrogen absorbed in the starting 5-nitro compound in an amount of 2 mols per mol of the 5-nitro compound. The resultant solution was heated to 100° C. and subjected to filtration under hot conditions for separation of the catalyst therefrom, followed by distilling off butanol for condensation. The condensed solution was allowed to cool to precipitate crystals, which were then separated by filtration, washed with water and dried to obtain 6.1 grams of 1-aminoanthraquinone having a purity of 98.5%.

When the above process was repeated using 11 grams of sodium tertiary phosphate instead of sodium carbonate, similar results were obtained.

EXAMPLE 16

0.1 Gram of a 5% palladium on carbon catalyst and 10 grams of a 20% aqueous sodium hydroxide solution were added to a mixture of 12.8 grams of 5-nitrotetrahydroanthraquinone and 170 grams of dipropylene glycol in an autoclave, into which was fed hydrogen, until the pressure reached 25 kg/cm$^2$, for hydrogenation of the 5-nitro compound at 120° C. with agitation. Hydrogen was absorbed in the starting 5-nitro compound in an amount of 2mols per mol of the 5-nitro compound. After completion of the hydrogenation, the resultant solution was subjected to filtration under hot conditions at 120° to 130° C. to remove the catalyst therefrom. To the resultant filtrate was added 350 grams of water for dilution to obtain crystals which were separated by filtration, washed with water and dried to yield 9.7 grams of 1-aminoanthraquinone having a purity of 96.7%.

EXAMPLE 17

1.4 Grams of 5% palladium on carbon catalyst and 52 grams of piperidine were added to a mixture of 154 grams of 5-nitrotetrahydroanthraquinone and 3,000 grams of methyl cellosolve, into which was fed hydrogen at room temperature and under normal pressure for having hydrogen absorbed in the starting 5-nitro compound in an amount of 2 mols per mol of the 5-nitro compound. After completion of the hydrogenation, the catalyst was separated by filtration and air was fed into the resultant filtrate at normal temperature for 1 hour. Then, the resultant solution was concentrated by distilling off the methyl cellosolve until crystals began to precipitate. The thus concentrated solution was allowed to cool and the resultant crystals were separated by filtration, washed with water and dried to obtain 114 grams of 1-aminoanthraquinone having a purity of 98.0%.

When the process was repeated using 60 grams of triethylamine or 52 grams of morpholine instead of the piperidine, similar results were obtained.

EXAMPLE 18

3 Grams of a Raney nickel catalyst and 100 grams of a 20% aqueous sodium hydroxide solution were added to a mixture of 128 grams of 5-nitrotetrahydroanthraquinone and 1,700 grams of cyclohexanol, into which was fed hydrogen while agitating at 100° C. for having hydrogen absorbed in the starting 5-nitro compound in an amount of 2 mols per mol of the 5-nitro compound. After completion of hydrogenation, the catalyst was separated by filtration and air was passed into the resultant filtrate at 30° C. for 1 hour. The resultant solution was cooled to 10° C. to precipitate crystals, which were then separated by filtration, washed with water and dried to obtain 92 grams of 1-aminoanthraquinone having a purity of 98.2%.

EXAMPLE 19

0.026 Gram of a 5% palladium on carbon catalyst and 3.0 grams of a 20% aqueous sodium hydroxide solution were added to a mixture of 2.6 grams of 5-nitrotetrahydroanthraquinone and 101 grams of methyl cellosolve, into which was fed hydrogen for having hydrogen absorbed at room temperature under normal pressure in the 5-nitro compound in an amount of 1.1 mols per mol of the 5-nitro compound. A small amount of reddish brown crystals were precipitated. The reaction solution was subjected to filtration, followed by washing with methyl cellosolve. The filtrate and washings were combined together and neutralized with dilute sulfuric acid. Then, the resultant solution was concentrated under reduced pressure to obtain crystals which were separated by filtration, washed with methanol and then with water, and dried to obtain 2.5 grams of 1-aminoanthraquinone. The purity was 97.8% and the yield was 93.3%.

In oxidation of the leuco type compounds produced by absorption of hydrogen in an amount greater than the theoretical during the hydrogenation reaction, in addition to air, oxygen and hydrogen peroxide, other oxidizing agents which may be used include perbenzoic acid, tert-butyl peroxide, sodium peroxide, potassium dichromate and the like.

What is claimed is:

1. A process for the preparation of 1-aminoanthraquinone, comprising catalytically hydrogenating 5-nitro-1,4,4a,9a-tetrahydroanthraquinone in a polar organic solvent in the presence of a hydrogenation catalyst whereby from 1 to 3 mols of hydrogen is allowed to be absorbed in each mol of said 5-nitro-1,4,4a,9a-tetrahydroanthraquinone; adding a base to the reaction system during or after completion of the hydrogenation reaction for further self oxidation and reduction reaction; and, when hydrogen is absorbed in an amount greater than the theoretical, oxidizing the resultant leuco type compound of 1-aminoanthraquinone with air or an oxidizing agent.

2. The process according to claim 1 wherein said hydrogenation catalyst is first introduced into the reaction system for the hydrogenation reaction whereby from 1.1 to 2.5 mols of hydrogen is allowed to be absorbed in each mol of said 5-nitro-1,4,4a,9a-tetrahydroanthraquinone, and then said base is introduced into the reaction system after completion of said hydrogenation.

3. The process according to claim 1 wherein said hydrogenation catalyst and said base are introduced into the reaction system at the same time for said hydrogenation reaction whereby from 1.1 to 2.2 mols of hydrogen is allowed to be absorbed in each mol of said 5-nitro-1,4,4a,9a-tetrahydroanthraquinone and for said self oxidation and reduction reaction.

4. The process according to claim 3 wherein said base is an alkali hydroxide and is used in an amount greater than 0.5 mol per mol of said 5-nitro-1,4,4a,9a-tetrahydroanthraquinone.

5. The process according to claim 1 wherein said 5-nitro-1,4,4a,9a-tetrahydroanthraquinone is used as the reaction solution obtained by reacting 5-nitro-1,4-naphthoquinone with 1,3-butadiene in a polar organic solvent.

6. The process according to claim 5 wherein said hydrogenation catalyst is palladium supported on a carbon carrier and said polar organic solvent is selected from the group consisting of β-hydroxyethyl methyl ether, β-hydroxydiethyl ether, diethylene glycol monomethyl ether, diethylene glycol monoethyl ether and methoxybutanol.

7. The process according to claim 1 wherein said hydrogenation catalyst is palladium supported on a carbon carrier.

8. The process according to claim 1 wherein said polar organic solvent is selected from the group consisting of β-hydroxyethyl methyl ether, β-hydroxydiethyl ether, diethylene glycol monomethyl ether, diethylene glycol monoethyl ether, and methoxybutanol.

9. The process according to claim 1 further comprising oxidizing the resultant reaction solution with air or an oxidizing agent.

10. The process according to claim 1 wherein the reaction is conducted at a temperature of from 0° to 160° C. and at a pressure of from normal atmospheric pressure to about 100 kg/cm$^2$ whereby from 1 to 3 mols of hydrogen is absorbed in each mol of 5-nitro-1,4,4a,9a-tetrahydroanthraquinone.

11. The process according to claim 2 wherein said hydrogenation is conducted at a temperature of from 10° to 120° C. and at a pressure of from normal atmospheric pressure to 100 kg/cm$^2$, said self oxidation and reduction is conducted at a temperature of from 20° to less than the boiling point of said polar organic solvent employed, and said oxidation of the leuco type compound of 1-aminoanthraquinone is conducted at a temperature of from 0° to 150° C.

12. The process according to claim 2 wherein said hydrogenation catalyst is removed from the reaction system by filtration either before the addition of said base to the reaction solution or after the reaction with the said base.

13. The process according to claim 3 wherein said hydrogenation and said self oxidation and reduction reaction are conducted at a temperature of from 10° to 120° C. and at a pressure of from normal pressure to 100 kg/cm$^2$, and said oxidation of the leuco type compound of 1-aminoanthraquinone is conducted at a temperature of from 0° to 150° C.

14. The process according to claim 6 wherein said hydrogenation catalyst is employed in an amount of from 0.002 to 0.5 parts by weight of catalyst, calculated in terms of palladium, per 100 parts of the 5-nitro-1,4,4a,9a-tetrahydroanthraquinone, and said polar organic solvent is employed in an amount of from 5 to 100 parts by weight per part of 5-nitro-1,4,4a,9a-tetrahydroanthraquinone.

15. The process according to claim 7 wherein said hydrogenation catalyst is employed in an amount of from 0.002 to 0.5 part by weight of catalyst, calculated in terms of palladium, per 100 parts of the 5-nitro-1,4,4a,9a-tetrahydroanthraquinone.

16. The process according to claim 8 wherein said polar organic solvent is employed in an amount of from 5 to 100 parts by weight per 100 parts of the 5-nitro-1,4,4a,9a-tetrahydroanthraquinone.

* * * * *